(12) United States Patent
Narasimhan

(10) Patent No.: US 11,868,902 B2
(45) Date of Patent: *Jan. 9, 2024

(54) TARGETED DATA RETRIEVAL AND DECISION-TREE-GUIDED DATA EVALUATION

(71) Applicant: Optum, Inc., Minnetonka, MN (US)

(72) Inventor: Ravi Narasimhan, Cypress, CA (US)

(73) Assignee: Optum, Inc., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/823,584

(22) Filed: Aug. 31, 2022

(65) Prior Publication Data
US 2023/0004818 A1 Jan. 5, 2023

Related U.S. Application Data

(63) Continuation of application No. 16/797,398, filed on Feb. 21, 2020, now Pat. No. 11,488,027.

(51) Int. Cl.
| | |
|---|---|
| *G16H 10/60* | (2018.01) |
| *G06N 5/01* | (2023.01) |
| *G06N 5/04* | (2023.01) |
| *G16H 50/20* | (2018.01) |

(52) U.S. Cl.
CPC .............. *G06N 5/01* (2023.01); *G06N 5/04* (2013.01); *G16H 10/60* (2018.01); *G16H 50/20* (2018.01)

(58) Field of Classification Search
CPC ..................................................... G06F 40/205
See application file for complete search history.

(56) References Cited

U.S. PATENT DOCUMENTS

| | | | |
|---|---|---|---|
| 6,188,988 B1 | 2/2001 | Barry et al. | |
| 7,693,727 B2 | 4/2010 | Moore | |
| 8,265,961 B2 | 9/2012 | Callas | |
| 8,296,163 B2 | 10/2012 | Fishman | |
| 8,635,599 B2 | 1/2014 | Velarde et al. | |
| 8,793,146 B2 | 7/2014 | Bonissone et al. | |
| 9,734,478 B2 | 8/2017 | Alhimiri | |
| 9,734,512 B2 | 8/2017 | Alhimiri | |
| 9,836,183 B1 * | 12/2017 | Love | G06F 16/904 |
| 9,852,473 B2 | 12/2017 | Richardson et al. | |

(Continued)

OTHER PUBLICATIONS

U.S. Appl. No. 16/797,398, filed Feb. 21, 2020, 2021/0264289, Allowed.

*Primary Examiner* — Di Xiao
(74) *Attorney, Agent, or Firm* — Alston & Bird LLP

(57) ABSTRACT

There is a need for more effective and efficient data evaluation. This need can be addressed by, for example, techniques for data evaluation in accordance with a shared decision tree data object. In one example, a method includes generating, using a plurality of feature extraction threads, shared evidentiary data; generating, based on a selected shared evidentiary data subset of the shared evidentiary data that correspond to one or more selected nodes of the shared decision tree data object, refined evidentiary data; processing the refined evidentiary data in accordance with the shared decision tree data object to generate an evaluation output and an explanation output; and displaying an evaluation output user interface comprising user interface data describing the evaluation output and the explanation output.

20 Claims, 13 Drawing Sheets

(56) References Cited

U.S. PATENT DOCUMENTS

| | | | |
|---|---|---|---|
| 2004/0267566 A1* | 12/2004 | Badgett | G06F 16/951 |
| | | | 707/E17.108 |
| 2009/0030290 A1 | 1/2009 | Kozuch et al. | |
| 2012/0166212 A1 | 6/2012 | Campbell | |
| 2013/0110755 A1 | 5/2013 | Upadhyayula et al. | |
| 2014/0277921 A1* | 9/2014 | Gujjar | G05B 23/0221 |
| | | | 701/32.9 |
| 2014/0330792 A1* | 11/2014 | Bhatt | G06F 16/353 |
| | | | 707/690 |
| 2018/0247023 A1 | 8/2018 | Divine et al. | |
| 2019/0065970 A1 | 2/2019 | Bonutti et al. | |
| 2019/0392950 A1 | 12/2019 | Conroy | |
| 2020/0257735 A1* | 8/2020 | Alter | G06F 16/986 |
| 2021/0158922 A1* | 5/2021 | Mahajan | G16H 20/10 |

\* cited by examiner

Criteria for Myocardial Perfusion Imaging

Myocardial positron emission tomography (PET), with or without simultaneous computed tomography (PET-CT), may be indicated for 1 or more of the
- Coronary artery disease assessment, [A] as indicated by 1 or more of the following(12)(13)(14)(15): [N]
  - Asymptomatic patient with elevated troponin level
  - Asymptomatic patient with ischemic changes present on resting ECG
  - Congenital heart disease, known (eg, repaired aortic coarctation, previous coronary reimplantation surgery, coronary artery compression)(36)
  - Exercise treadmill test results equivocal or positive, requiring further evaluation
  - Need for ischemic evaluation, as indicated by ALL of the following:
    - Clinically significant coronary artery disease, as indicated by 1 or more of the following:
      ○ Anomalous coronary artery, known, and need for functional assessment(35)
      ○ Before revascularization (ie, percutaneous coronary intervention or coronary artery bypass grafting) to demonstrate ischemia
      ○ Coronary calcium Agatston score between 10 and 400 on cardiac CT scan, and high risk for coronary heart disease, as indicated t
        - Calculated 10-year absolute coronary heart disease risk greater than 20% by global risk calculator(41)
        - Coronary heart disease risk equivalent (eg, peripheral arterial disease, carotid artery disease, or abdominal aortic aneurysm)
        - Diabetes mellitus in patient age 40 years or older
        - Prior stroke or transient ischemic attack(42)

Exercise treadmill testing alone is or would be unreliable or inconclusive due to 1 or more of the following(12)(48):
      ○ Anginal symptoms induced by exercise in high-risk patient without any diagnostic ECG changes on previous exe
      ○ Atrial fibrillation or flutter
      ○ Electronically paced ventricular rhythm
      ○ Insufficient workload (ie, inability to achieve at least 85% of maximum age-sex predicted heart rate on Bruce pro
      ○ Left bundle branch block
      ○ Left ventricular hypertrophy with repolarization abnormalities on baseline ECG
      ○ Patient taking digoxin
      ○ Pre-excitation syndrome (eg, Wolff-Parkinson-White syndrome)
      ○ ST segment on baseline ECG with 1 mm depression or greater ○ Myocardial viability assessment, [B] as indicated by 1 or more of the following(33): [N]
    - Chronic secondary mitral regurgitation, and patient is candidate for revascularization if viable myocardi
    - Ischemic cardiomyopathy, known or suspected, with left ventricular ejection fraction 35% or less(4)
    - Preoperative or preprocedural planning needed for revascularization (ie, coronary artery bypass graft o
    - SPECT myocardial perfusion scan or stress echocardiogram findings inconclusive, or no viable myocar
  ○ Prosthetic valve endocarditis, suspected, as indicated by ALL of the following (59)(60)(61)(62)(63): [N]
    - Clinical suspicion of endocarditis
    - Echocardiogram results are nondiagnostic
    - Prosthetic valve implanted more than 3 months earlier

FIG. 12

CLINICAL NOTES

In the next couple days, you will receive an emailed survey requesting feedback about your visit today. We use this information to improve processes and systems, and to reward and recognize our staff that assisted you today in your visit.

Your Medical Assistant today was Jamie.

Thank you in advance, for your time!

Recommendations:

1. Medications:Continue current medications.

*Management of Neuropsychiatric Symptoms (PQRS #284):* Continue current medications used for neuropsychiatric symptoms.

2. Medical studies and referrals:

*Blood Tests:* CBC, CMP, TSH, B12

*Imaging:* An FDG-PET scan will be requested to complete this patient's evaluation if after a comprehensive evaluation the cause of symptoms remains uncertain. Cognitive decline has been present for at least 6 months. A dementia syndrome is present and clinical criteria are met for both Alzheimer's disease and frontotemporal dementia. *and amyloid PET scan in IDEAS study*

*Neuropsychological testing:* None

1302

MEDICAL CLAIMS

| ENTY_NM | CLM_HEAD_ID | SBSCR_ID | SRVC_PROV_ID | SRVC_PROV_SPCL |
|---|---|---|---|---|
| OMN-AZ | 12003831 0000 | | F06400002848 | FAMP |
| OMN-AZ | 120901535E00 | | F06400002848 | FAMP |
| OMN-AZ | 120871582E00 | | A02900031485 | INTM |
| OMN-AZ | 120871583E00 | | A02900031485 | INTM |
| OMN-AZ | 120871584E00 | | A02900031485 | INTM |
| OMN-AZ | 120861566E00 | | F06400002848 | FAMP |
| OMN-AZ | 120861566E00 | | F06400002848 | FAMP |
| OMN-AZ | 120832045E00 | | A02900031485 | INTM |

1301

RX

| ENTY_NM | SBSCR_NBR | DT_OF_SRVC | DRG_BRND_NM | QTY |
|---|---|---|---|---|
| OMN-AZ | | 2017-02-06 00:00:00.000 | VALSARTAN | 90.00 |
| OMN-AZ | | 2017-07-09 00:00:00.000 | VALSARTAN-HYDROCHLOROTHIAZIDE | 30.00 |
| OMN-AZ | | 2017-10-29 00:00:00.000 | VALSARTAN-HYDROCHLOROTHIAZIDE | 30.00 |
| OMN-AZ | | 2016-08-14 00:00:00.000 | FLUARIXQUAD 2016-2017 | 1.00 |
| OMN-AZ | | 2017-03-29 00:00:00.000 | ACETAMINOPHEN-CODEINE | 90.00 |
| OMN-AZ | | 2017-07-12 00:00:00.000 | TRAMADOL HCL | 180.00 |
| OMN-AZ | | 2017-10-04 00:00:00.000 | TRAMADOL HCL | 180.00 |
| OMN-AZ | | 2017-11-15 00:00:00.000 | PROGESTERONE | 90.00 |
| OMN-AZ | | 2016-06-21 00:00:00.000 | NA | 3.00 |

1304

LAB RESULTS

| ENTY_NM | UNQ_MER_ID | SBSCR_NBR | SRVC_DT | LAB_TST_NM | LONC_CD | LAB_RSLT_TXT | LAB_RSLT_NBR |
|---|---|---|---|---|---|---|---|
| OMN-AZ | | | 2017-02-20 00:00:00.000 | CALCIUM, SERUM | 17861-6 | NULL | 8.830000 |
| OMN-AZ | | | 2016-05-13 00:00:00.000 | GLUCOSE, SERUM | 2345-7 | NULL | 102.000000 |
| OMN-AZ | | | 2017-08-19 00:00:00.000 | GLUCOSE, SERUM | 2345-7 | NULL | 116.000000 |
| OMN-AZ | | | 2017-02-20 00:00:00.000 | BUN | 3094-0 | NULL | 11.000000 |
| OMN-AZ | | | 2016-09-13 00:00:00.000 | CHOLESTEROL TOTAL | 2093-3 | NULL | 138.000000 |
| OMN-AZ | | | 2016-12-05 00:00:00.000 | PROTEIN, TOTAL SERUM | 2885-2 | NULL | 6.930000 |
| OMN-AZ | | | 2017-12-05 00:00:00.000 | PROTEIN, TOTAL SERUM | 2885-2 | NULL | 7.100000 |
| OMN-AZ | | | 2017-05-22 00:00:00.000 | ALBUMIN, SERUM | 1751-7 | NULL | 3.900000 |

TARGETED DATA RETRIEVAL AND DECISION-TREE-GUIDED DATA EVALUATION

CROSS-REFERENCE TO RELATED APPLICATIONS

This application is a continuation of U.S. Non-Provisional application Ser. No. 16/797,398, filed Feb. 21, 2020, the contents of which are hereby incorporated herein in its entirety by reference.

BACKGROUND

Various embodiments of the present invention address technical challenges related to performing data evaluation. Various embodiments of the present invention disclose innovative techniques for performing data evaluation using targeted data retrieval and decision-tree-guided data evaluation.

BRIEF SUMMARY

In general, embodiments of the present invention provide methods, apparatuses, systems, computing devices, computing entities, and/or the like for performing targeted data retrieval and decision-tree-guided data evaluation. Various embodiments of the present invention disclose techniques for performing targeted data retrieval and decision-tree-guided data evaluation that utilize at least one of structured feature extraction threads, unstructured feature extraction threads, shared feature processing interfaces, feature extraction engines, evidence refinement engines, and shared decision tree data objects.

In accordance with one aspect, a method is provided. In one embodiment, the method comprises generating, using a plurality of feature extraction threads, shared evidentiary data, wherein generating the evidentiary data comprises: identifying one or more structured feature extraction threads of the plurality of feature extraction threads and one or more unstructured feature extraction threads of the plurality of feature extraction threads; causing each structured feature extraction thread of the one or more structured feature extraction threads to extract corresponding per-source retrieved feature data from a corresponding structured data source of one or more structured data sources that is associated with the structured feature extraction thread; causing each unstructured feature extraction thread of the one or more unstructured feature extraction threads to (i) extract corresponding per-source unstructured feature data from a corresponding unstructured data source of one or more unstructured data sources that is associated with the unstructured feature extraction thread, and (ii) process the corresponding per-source unstructured feature data for the unstructured feature extraction thread to generate per-source engineered feature data for the unstructured feature extraction thread; and aggregating each per-source retrieved feature data extracted by a structured feature extraction thread of the one or more structured feature extraction threads and each per-source engineered feature data generated by an unstructured feature extraction thread of the one or more unstructured feature extraction threads to generate the evidentiary data; generating, based on a selected evidentiary data subset of the shared evidentiary data that correspond to one or more selected nodes of the shared decision tree data object, refined evidentiary data; processing the refined evidentiary data in accordance with the shared decision tree data object to generate an evaluation output and an explanation output; and providing, for display via a user interface, at least a portion of the evaluation output comprising user interface data indicative of the evaluation output and the explanation output.

In accordance with another aspect, a computer program product is provided. The computer program product may comprise at least one computer-readable storage medium having computer-readable program code portions stored therein, the computer-readable program code portions comprising executable portions configured to generate, using a plurality of feature extraction threads, shared evidentiary data, wherein generating the evidentiary data comprises: identifying one or more structured feature extraction threads of the plurality of feature extraction threads and one or more unstructured feature extraction threads of the plurality of feature extraction threads; causing each structured feature extraction thread of the one or more structured feature extraction threads to extract corresponding per-source retrieved feature data from a corresponding structured data source of one or more structured data sources that is associated with the structured feature extraction thread; causing each unstructured feature extraction thread of the one or more unstructured feature extraction threads to (i) extract corresponding per-source unstructured feature data from a corresponding unstructured data source of one or more unstructured data sources that is associated with the unstructured feature extraction thread, and (ii) process the corresponding per-source unstructured feature data for the unstructured feature extraction thread to generate per-source engineered feature data for the unstructured feature extraction thread; and aggregating each per-source retrieved feature data extracted by a structured feature extraction thread of the one or more structured feature extraction threads and each per-source engineered feature data generated by an unstructured feature extraction thread of the one or more unstructured feature extraction threads to generate the evidentiary data; generate, based on a selected evidentiary data subset of the shared evidentiary data that correspond to one or more selected nodes of the shared decision tree data object, refined evidentiary data; process the refined evidentiary data in accordance with the shared decision tree data object to generate an evaluation output and an explanation output; and provide, for display via a user interface, at least a portion of the evaluation output comprising user interface data indicative of the evaluation output and the explanation output.

In accordance with yet another aspect, an apparatus comprising at least one processor and at least one memory, including computer program code, is provided. In one embodiment, the at least one memory and the computer program code may be configured to, with the processor, cause the apparatus to generate, using a plurality of feature extraction threads, shared evidentiary data, wherein generating the evidentiary data comprises: identifying one or more structured feature extraction threads of the plurality of feature extraction threads and one or more unstructured feature extraction threads of the plurality of feature extraction threads; causing each structured feature extraction thread of the one or more structured feature extraction threads to extract corresponding per-source retrieved feature data from a corresponding structured data source of one or more structured data sources that is associated with the structured feature extraction thread; causing each unstructured feature extraction thread of the one or more unstructured feature extraction threads to (i) extract corresponding per-source unstructured feature data from a corresponding unstructured data source of one or more unstructured data sources that is associated with the unstructured feature extraction thread, and (ii) process the corresponding per-source unstructured feature data for the unstructured feature extraction thread to generate per-source engineered feature data for the unstructured feature extraction thread; and aggregating each per-source retrieved feature data extracted by a structured feature extraction thread of the one or more structured feature extraction threads and each per-source engineered feature data generated by an unstructured feature extraction thread of the one or more unstructured feature extraction threads to generate the evidentiary data; generate, based on a selected evidentiary data subset of the shared evidentiary data that correspond to one or more selected nodes of the shared decision tree data object, refined evidentiary data; process the refined evidentiary data in accordance with the shared decision tree data object to generate an evaluation output and an explanation output; and provide, for display via a user interface, at least a portion of the evaluation output comprising user interface data indicative of the evaluation output and the explanation output.

BRIEF DESCRIPTION OF THE DRAWINGS

Figure 1:
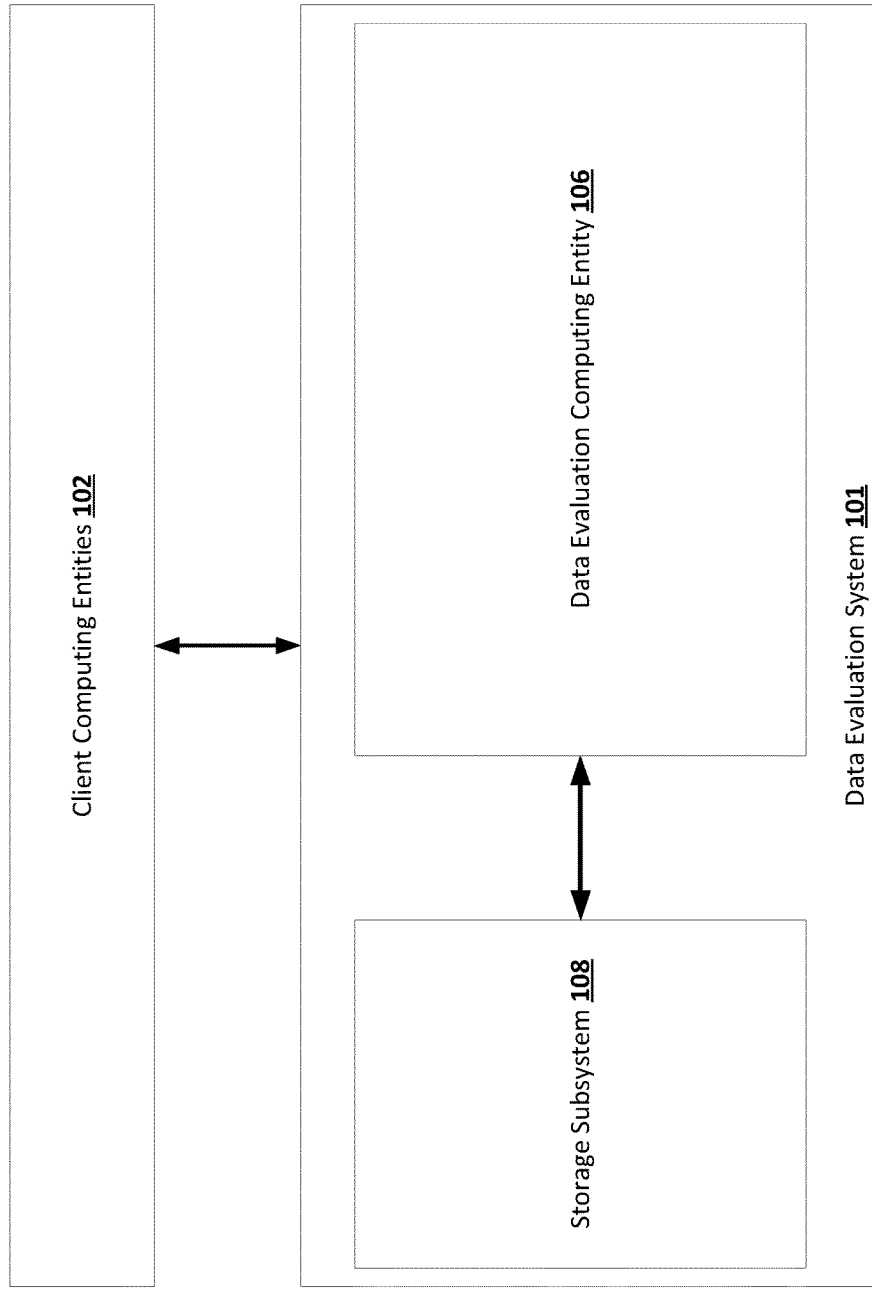

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
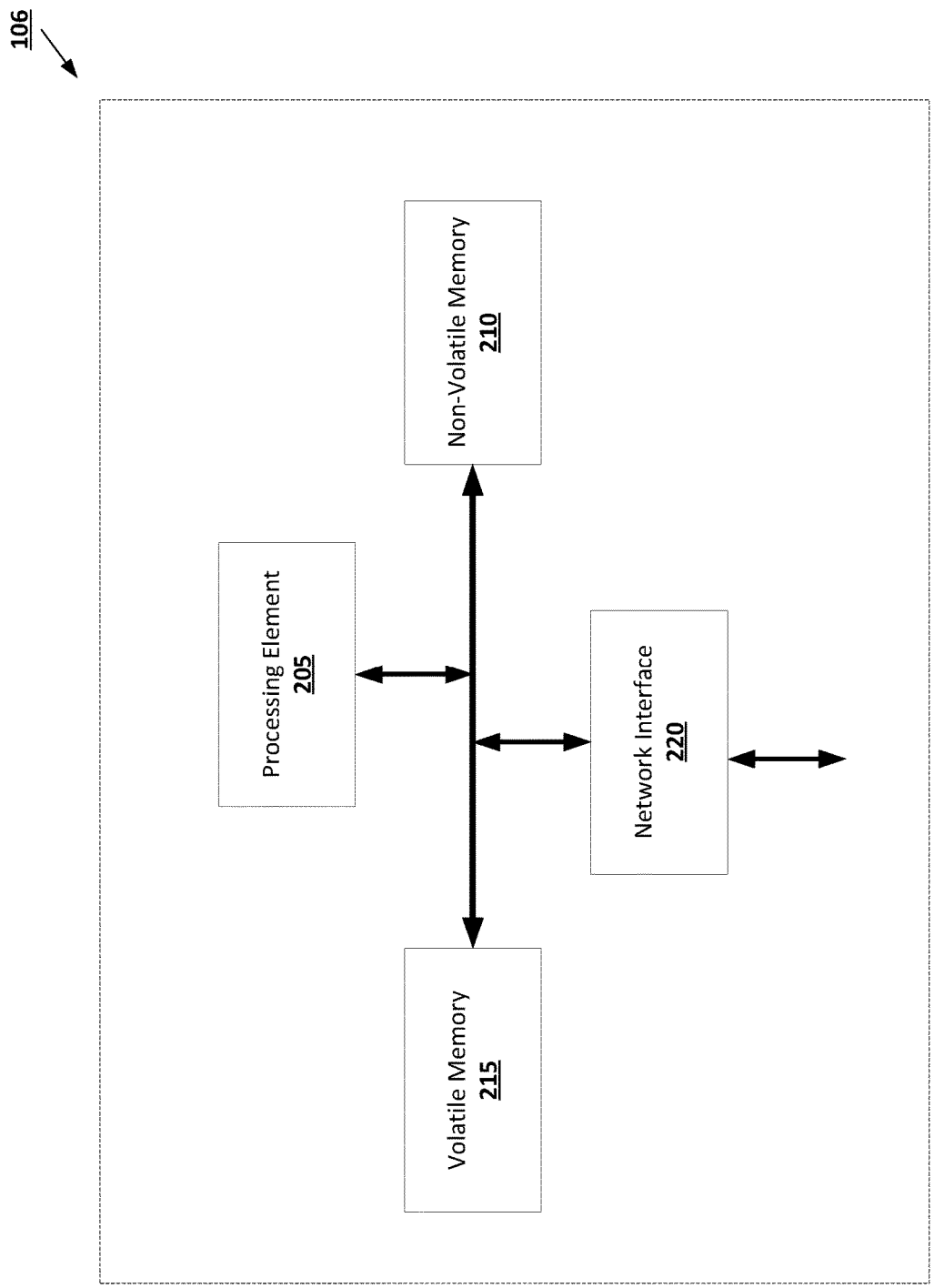

FIG. 2 provides an example data evaluation computing entity in accordance with some embodiments discussed herein.

Figure 3:
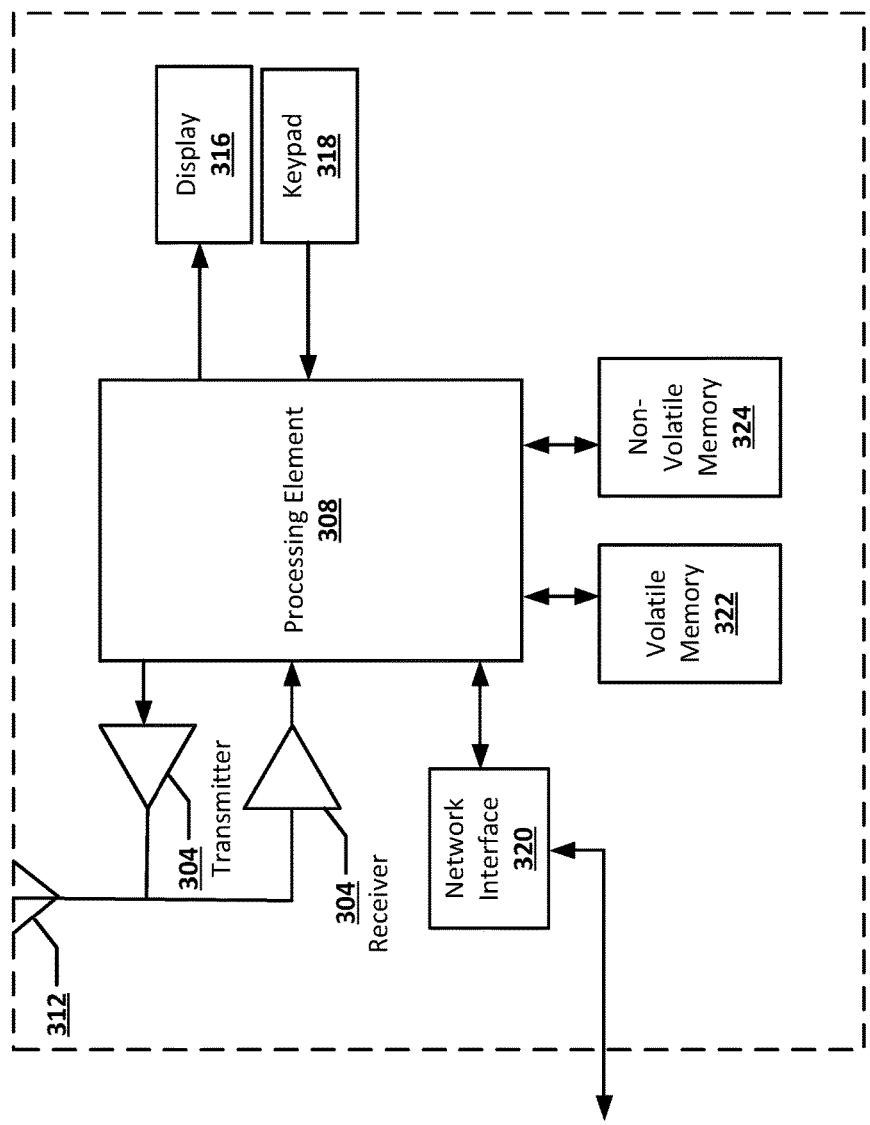

FIG. 3 provides an example client computing entity in accordance with some embodiments discussed herein.

Figure 4:
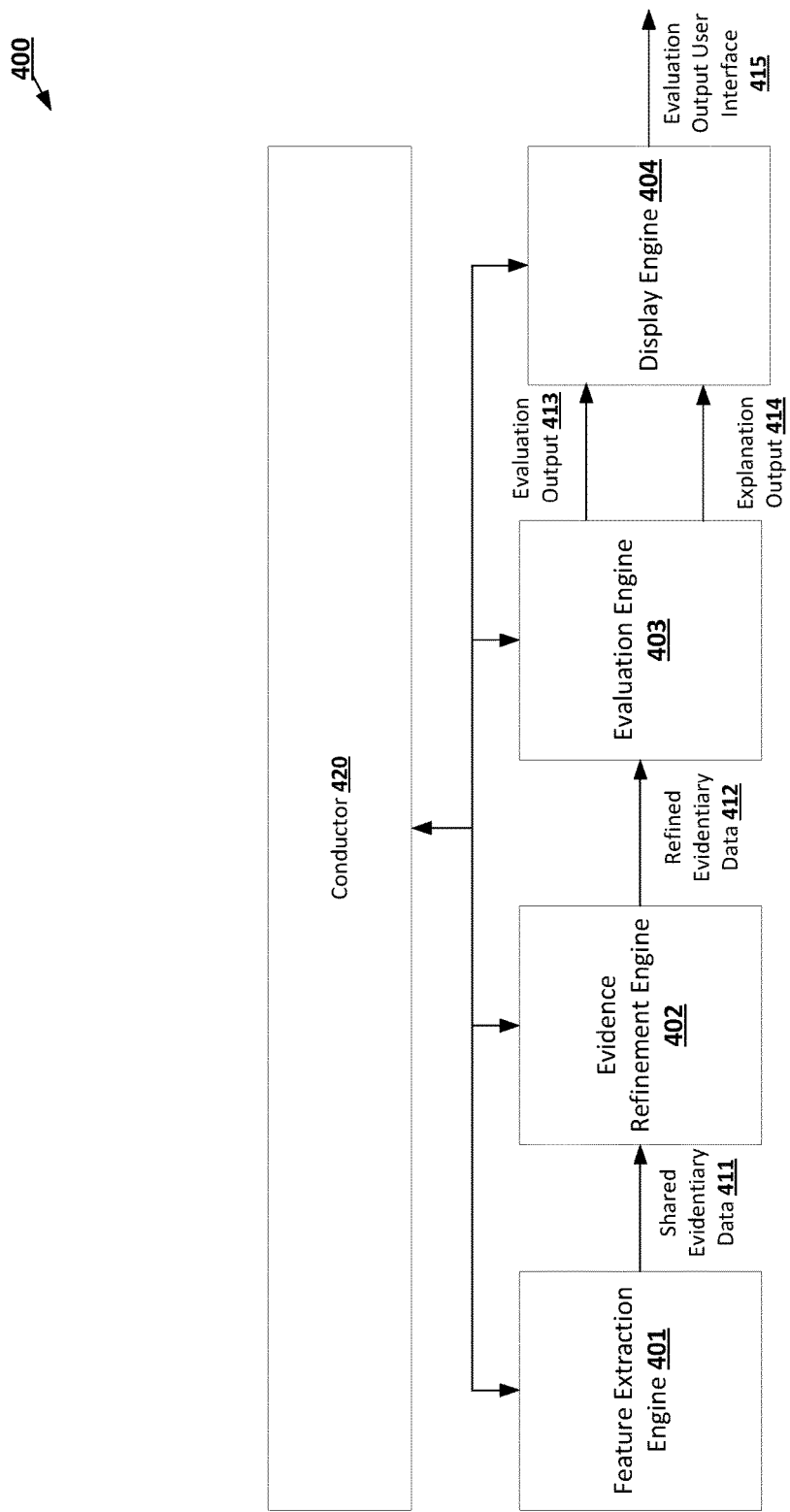

FIG. 4 is a data flow diagram of an example process for performing data evaluation using a shared decision tree data object in accordance with some embodiments discussed herein.

Figure 5:
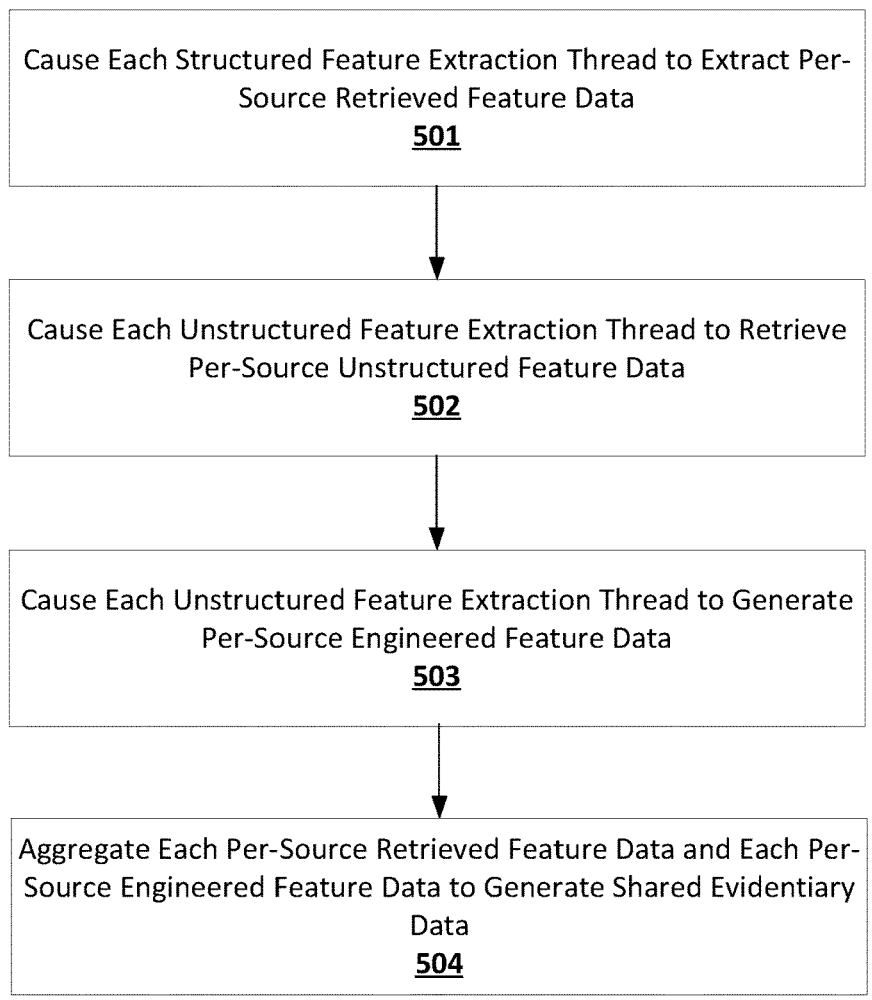

FIG. 5 is a flowchart diagram of an example process for generating shared evidentiary data in accordance with some embodiments discussed herein.

Figure 6:
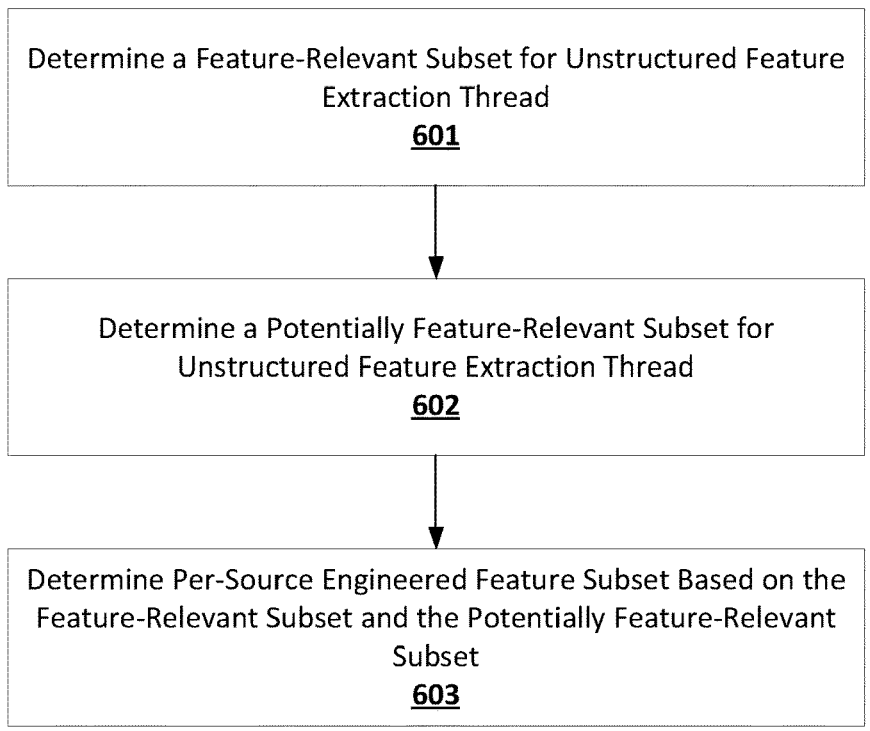

FIG. 6 is a flowchart diagram of an example process for causing an unstructured feature extraction thread to process per-source unstructured feature data to generate per-source engineered feature data in accordance with some embodiments discussed herein.

Figure 7:
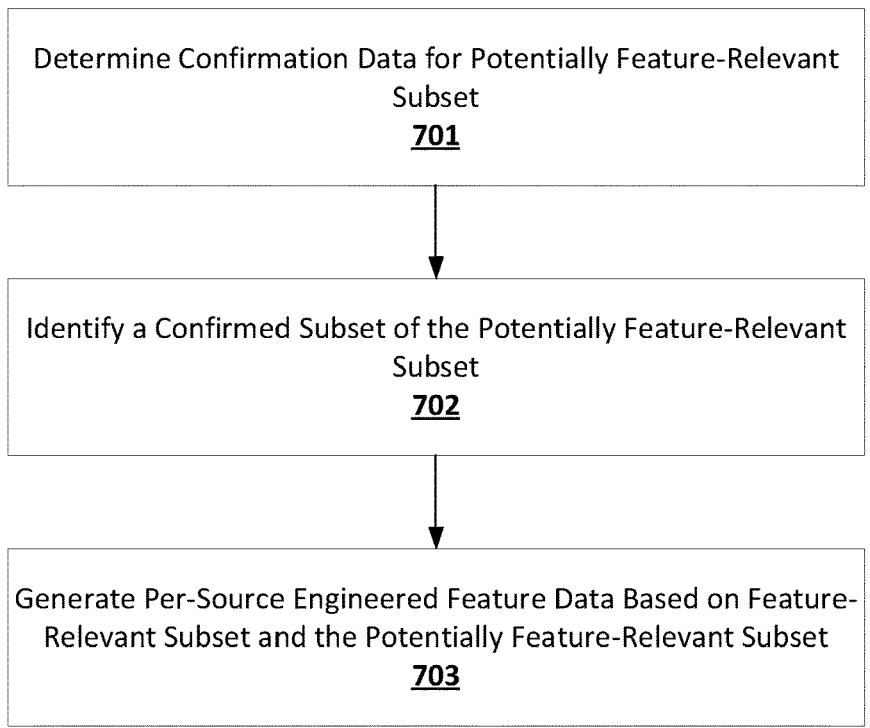

FIG. 7 is a flowchart diagram of an example process for generating per-source engineered feature data for an unstructured feature extraction thread in accordance with some embodiments discussed herein.

Figure 8:
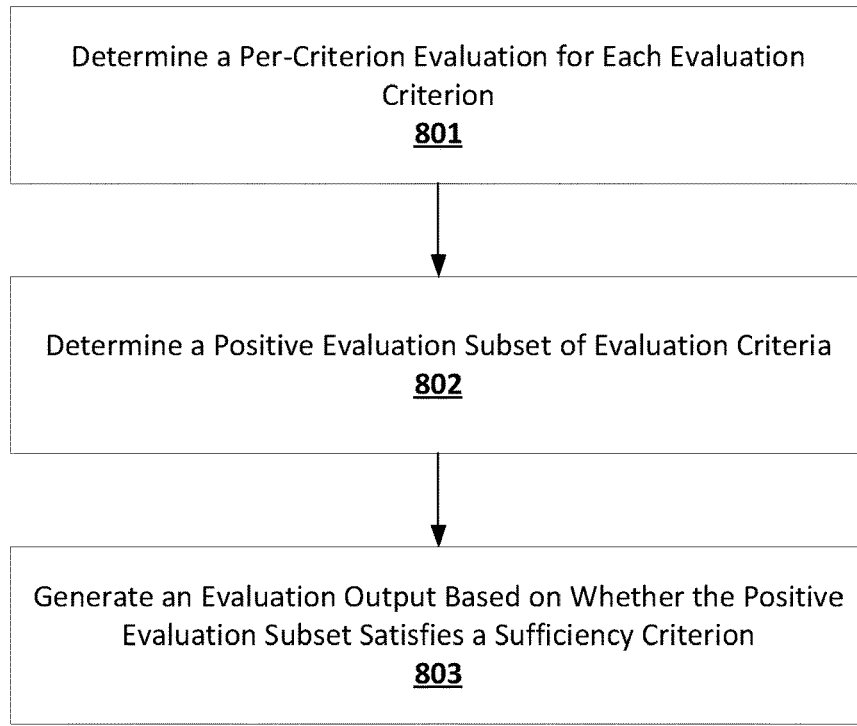

FIG. 8 is a flowchart diagram of an example process for generating an evidentiary output in accordance with some embodiments discussed herein.

Figure 9:
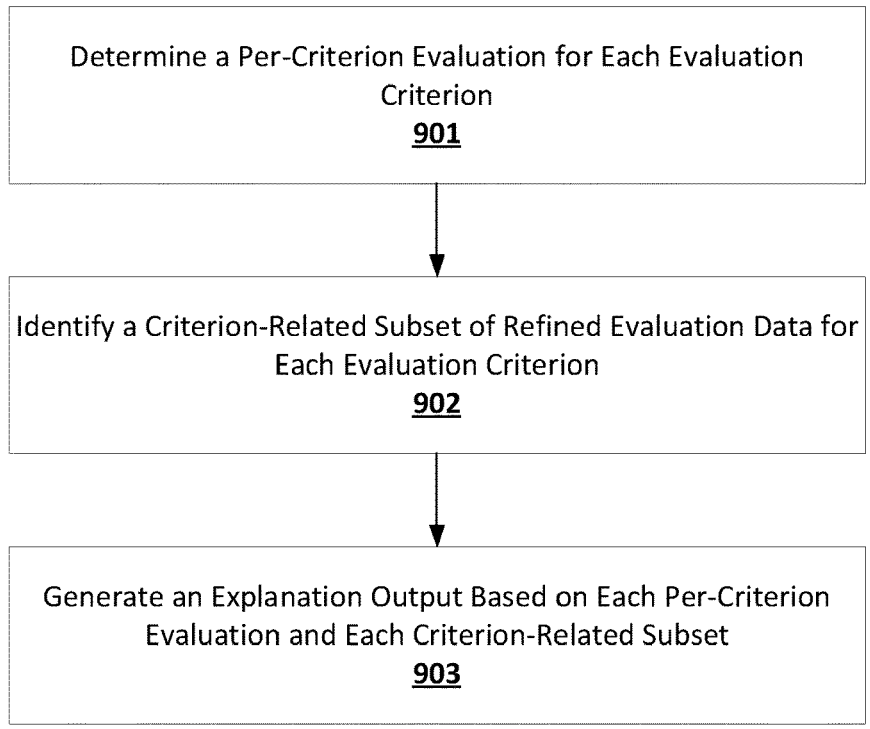

FIG. 9 is a flowchart diagram of an example process for generating an explanation output in accordance with some embodiments discussed herein.

Figure 10:

FIG. 10 provides an operational example of an evaluation output user interface in accordance with some embodiments discussed herein.

Figure 11:
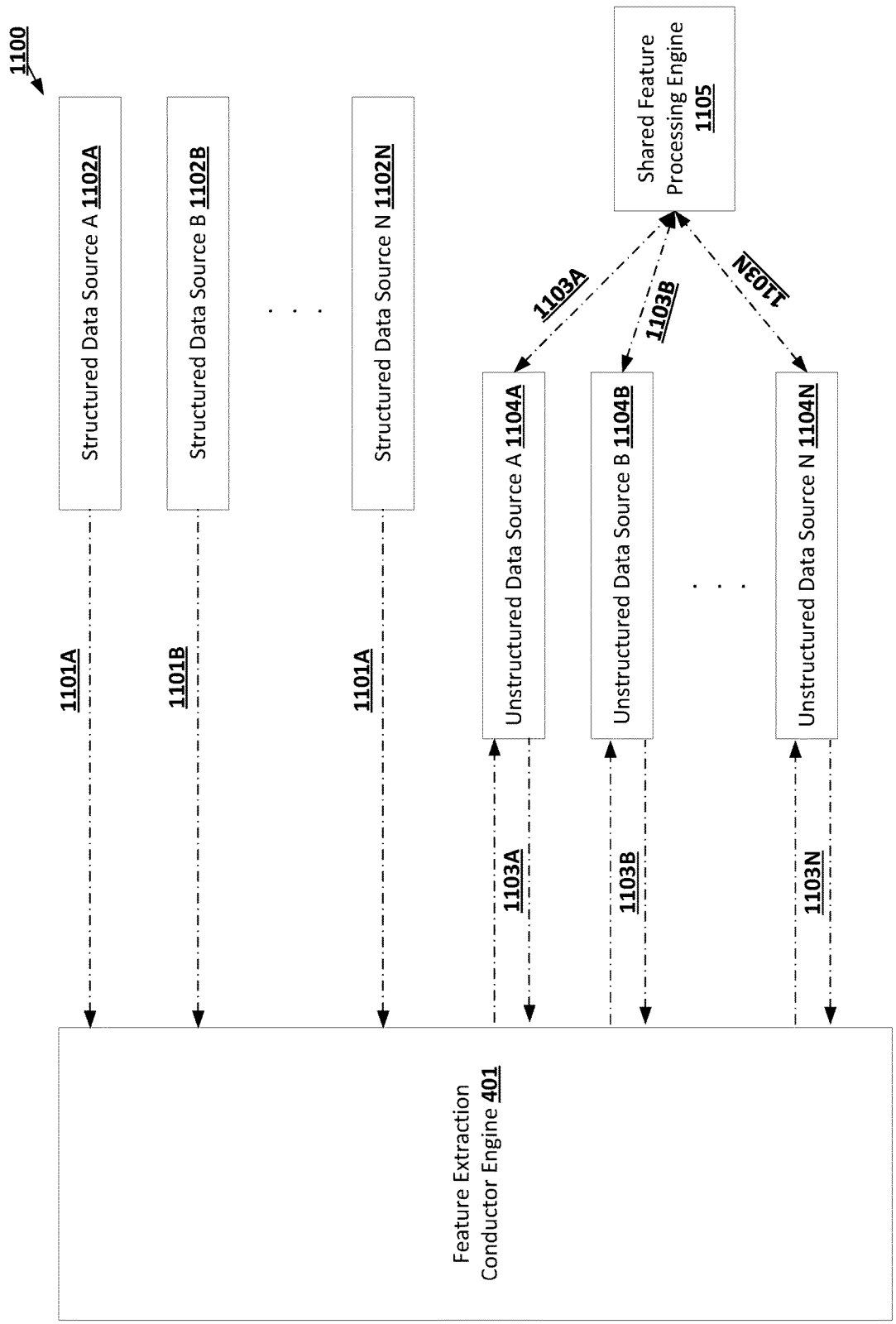

FIG. 11 provides an operational example of a process for thread coordination by a feature extraction engine in accordance with some embodiments discussed herein.

FIG. 12 provides an operational example of evaluation criteria data in accordance with some embodiments discussed herein.

FIG. 13 provides operational examples of data sources of various types in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview

Various embodiments of the present invention improve efficiency of performing data evaluation by disclosing techniques that enable targeted data retrieval in order to decrease the amount of data needed to be retrieved prior to performing data evaluation. For example, in some embodiments, a data retrieval engine may limit data retrieval to data deemed related to an input entity (e.g., a patient entity) associated with a particular data evaluation task. By limiting the amount of data needed to be retrieved prior to performing data evaluation, various embodiments of the present invention decrease the computational complexity of data retrieval tasks and (in circumstances where retrieval of data requires utilizing network communications) improve network efficiency of data evaluation architectures that utilize remote data sources. In doing so, various embodiments of the present invention improve efficiency of performing data evaluation.

Furthermore, various embodiments of the present invention address technical challenges related to efficiently and reliably performing data evaluation using distributed data evaluation environments. A distributed data evaluation environment is a software solution configured to perform a data evaluation task using input data retrieved from multiple data sources, often a very large number of data sources. An example of a distributed data evaluation environment is a software solution configured to generate prior authorization determinations for proposed medical operations based on data provided from medical-history-related data sources, medical-claim-related data sources, pharmaceutical-history-related data sources, medical-note-related data sources, and/or the like.

The diversity of input data sources in distributed data evaluation environments presents substantial challenges for software developers that intend to design and deploy data analysis software solutions in the noted distributed data evaluation environments. For example, without employing some degree of parallelism, evaluative data analysis would likely be very inefficient in distributed data evaluation environments because of the often large number of data sources in such distributed data evaluation environments, with the task of data retrieval from the data sources acting as an efficiency bottleneck on the system as a whole.

On the other hand, employing parallelism in such distributed data evaluation environments may lead to other challenges. For example, if the data extraction process is followed by some pre-processing on the data (as is very often the case), coordinating utilization of shared pre-processing resources among various execution in order to avoid deadlock situations threads may be challenging. Thus, various existing distributed data evaluation environments suffer from substantial efficiency and reliability challenges due to the technical challenges identified above as well as similar technical challenges.

Various embodiments of the present invention address the above-noted technical challenges related to efficiently and reliably performing data evaluation in distributed data evaluation environments by providing techniques for parallelized data evaluation that utilize a data-source-specific thread to extract data from each source. By utilizing data-source-specific feature extraction threads, the noted embodiments of the present invention prevent deadlock scenarios where multiple feature threads may attempt to extract data from the same data source and/or using the access interface of the same data source at the same time.

In addition, various embodiments of the present invention address the above-noted technical challenges related to efficiently and reliably performing data evaluation in distributed data evaluation environments by providing techniques for parallelized data evaluation that employ parallelism during data retrieval but limit post-retrieval data processing at the feature-extraction stage to extraction threads configured to retrieve unstructured data from unstructured data sources. By limiting post-retrieval data processing at the feature-extracting-thread level to execution threads configured to retrieve unstructured data from unstructured data sources, various embodiments of the present invention provide protocols for thread coordination that reduce the risk of deadlock scenarios in multi-threaded distributed data evaluation environments.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1A is a schematic diagram of an example architecture 100 for performing parallelized data evaluation. The architecture 100 includes a data evaluation system 101 configured to receive data evaluation requests the client computing entities 102, process the data evaluation requests to generate evaluation outputs and/or explanation outputs, provide evaluation output interfaces describing evaluation outputs and/or explanation outputs to the client computing entities 102, and/or perform evaluation-based actions based on evaluation outputs and/or explanation outputs. For example, the parallelized data evaluation system 107 may in some embodiments be configured to generate prior authorization determinations for proposed medical operations based on data provided from medical-history-related data sources, medical-claim-related data sources, pharmaceutical-history-related data sources, medical-note-related data sources, and/or the like.

In some embodiments, data evaluation system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The data evaluation system 101 may include a data evaluation computing entity 106 and a storage subsystem 108. The data evaluation computing entity 106 may be configured to process the data evaluation requests to generate evaluation outputs and/or explanation outputs, provide evaluation output interfaces describing evaluation outputs and/or explanation outputs to the client computing entities 102, and/or perform evaluation-based actions based on evaluation outputs and/or explanation outputs. The storage subsystem 108 may be configured to store at least a portion of input data utilized by the data evaluation computing entity 106 to perform parallelized predictive data analysis. The storage subsystem 108 may further be configured to store at least a portion of configuration data (e.g., model definition data) utilized by the data evaluation computing entity 106 to perform parallelized predictive data analysis.

The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Data Evaluation Computing Entity

FIG. 2 provides a schematic of a data evaluation computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the data evaluation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the data evaluation computing entity 106 may include or be in communication with one or more processing elements 205 (also referred to as processors, processing circuitry, and/or similar terms used herein interchangeably) that communicate with other elements within the data evaluation computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the data evaluation computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the data evaluation computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the data evaluation computing entity 106 with the assistance of the processing element 205 and operating system.

As indicated, in one embodiment, the data evaluation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data evaluation computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the data evaluation computing entity 106 may include or be in communication with one or more input elements, such as a keyboard input, a mouse input, a touch screen/display input, motion input, movement input, audio input, pointing device input, joystick input, keypad input, and/or the like. The data evaluation computing entity 106 may also include or be in communication with one or more output elements (not shown), such as audio output, video output, screen/display output, motion output, movement output, and/or the like.

Exemplary Client Computing Entity

FIG. 3 provides an illustrative schematic representative of a client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the data evaluation computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the data evaluation computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the data evaluation computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the data evaluation computing entity 106 and/or various other computing entities.

In another embodiment, the client computing entity 102 may include one or more components or functionality that are the same or similar to those of the data evaluation computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. Exemplary System Operations

As described below, various embodiments of the present invention relate to disclosing techniques for performing data evaluation in a parallelized manner. An exemplary application of the noted parallelized data evaluation concepts relate to determining prior authorization determinations for proposed medical operations. Aspects of the parallelized data evaluation concepts and the automated prior authorization determination concepts are described in greater detail below.

Various embodiments of the present invention utilize the parallelized data evaluation concepts described below to determine prior authorization determinations for proposed medical operations based at least in part on input data associated with corresponding patients related to the proposed medical operations. For example, in some embodiments, the data evaluation computing entity 106 may extract (e.g., using a parallelized data extraction procedure) evidentiary data describing patient history and/or patient demographics of a patient that is subject of a prior authorization task, refine the extracted evidentiary data in accordance with a decision tree data object that describes the pre-authorization requirements for generating a positive prior authorization determination for the noted prior authorization task in order to isolate portions of the extracted evidentiary that relate to the noted pre-authorization requirements, process the refined evidentiary data in accordance with the decision tree data object in order to determine a prior authorization determination for the proposed medical operation, aggregate the refined evidentiary data used to reach the prior authorization determination to generate an explanation output for the prior authorization determination, and present display data related to the prior authorization determination and the explanation output using a prior authorization user interface configured to display prior-authorization-related data to end-users (e.g., to physicians, nurses, hospital staff, and/or the like).

However, while various embodiments of the present invention describe the data evaluation concepts of the present invention in relation to prior authorization determination for proposed medical operations, a person of ordinary skill in the relevant technology will recognize that the data evaluation concepts can be utilized to perform any data evaluation task in an efficient and reliable manner.

FIG. 4 is a data flow diagram of an example process 400 for performing data evaluation of distributed evidentiary data in accordance a shared decision tree data object. Via the various steps/operations of the process 400, the data evaluation computing entity 106 can reduce occurrence likelihood of deadlock scenarios in predictive data analysis systems that utilize distributed input data sources, thus increasing the operational reliability of the noted predictive data analysis systems.

The process 400 begins when a feature extraction engine 401 of the data evaluation computing entity 106 generates shared evidentiary data 411 using a plurality of feature extraction threads. The shared evidentiary data 411 may include a collection of data objects that are deemed related to an input entity, where an input entity may be a data object that describes a real-world entity and/or a real-world phenomenon with respect to which data evaluation is performed. For example, the shared evaluation data may include medical history data of a patient input entity. The shared evidentiary data 411 may be generated based on input data stored on the storage subsystem 108 and/or storage data provided by a client computing entity 102.

The feature extraction engine 401 may generate the shared evidentiary data 411 based on data retrieved from a plurality of evidentiary data sources (not depicted). An evidentiary data source may be any storage platform and/or portion of a storage platform that stores at least one of one or more data assets including evidentiary data associated with one or more input entities. Examples of data sources include clinical data sources, medical claims data sources, lab results data sources, pharmaceutical history data sources, medical note data objects (e.g., physician-generated medical note data objects) and/or the like. In some embodiments, to retrieve data from the plurality of evidentiary data sources, the feature extraction engine 401 utilizes a plurality of feature extraction threads, where each feature extraction thread may be configured to retrieve evidentiary data associated with a target input entity from an evidentiary data source of the plurality of evidentiary data sources that is associated with the feature extraction thread.

In some embodiment, retrieval of data by the feature extraction threads is performed by data extraction policies that are defined in accordance with the data evaluation. For example, when a data evaluation pertains to a particular patient entity, the feature extraction threads may be configured to retrieve structured data and unstructured data deemed related to the particular patient entity. In some embodiments, retrieval of data by the feature extraction threads is performed by data extraction policies that are defined in accordance with at least a subset of nodes of a decision tree associated with the data evaluation. For example, when a data evaluation pertains to a medical data evaluation subject, the decision tree of the data evaluation may describe the medical data evaluation subject association of the data evaluation, and the threads may be configured to retrieve structured data and unstructured data deemed related to medical information of the particular patient entity.

In some embodiments, to generate the shared evidentiary data 411, the feature extraction engine 401 performs the steps/operations of the process depicted in FIG. 5. As depicted in FIG. 5, at step/operation 501, the feature extraction engine 401 causes each structured feature extraction thread of one or more feature extraction threads to extract corresponding retrieved feature data from corresponding structured data source of one or more structured data sources that is associated with the structured feature extraction thread. A structured data source may be a data source that stores structured data, where structured data may include a collection of data objects that are organized in a manner that clearly indicates the relationships between the data objects. Examples of structured data include data stored in at least one of relational databases, graph-based databases, object-oriented databases, and/or the like. A structured feature extraction thread may be a feature extraction thread that is configured to extract data from a structured data source that is associated with the structured feature extraction thread.

At step/operation 502, the feature extraction engine 401 causes each unstructured feature extraction thread of one or more unstructured feature extraction threads to extract corresponding unstructured feature data from an unstructured data source of one or more unstructured data sources. An unstructured data source may be a data source that stores unstructured data, where unstructured data may include a collection of data objects that are not organized in a manner that clearly indicates the relationships between the data objects. Examples of unstructured data include natural language data, such as natural language medical note data.

Operational examples of structured data sets and unstructured data sets are depicted in FIG. 13. FIG. 13 displays four data sets, three of which are structured data sets and one of which is an unstructured data set. In particular, the four sets displayed in FIG. 13 include a medical claims data set 1301 that is a structured data set, a clinical notes data set 1302 that is an unstructured natural language data set, a lab results data set 1303 that is a structured data set, and a pharmaceutical history data set 1304 that is a structured data set.

Returning to FIG. 5, at step/operation 503, the feature extraction engine 401 causes each unstructured feature extraction thread of the one or more unstructured feature extraction threads to process corresponding per-source unstructured feature data for the unstructured feature extraction thread using a shared feature processing interface to generate per-source engineered feature data for the unstructured feature extraction thread.

In some embodiments, the feature extraction engine 401 causes each unstructured feature extraction thread to utilize a shared feature processing interface accessible by all of the unstructured feature extraction threads in order to generate, based on the corresponding per-source unstructured feature data for the unstructured feature extraction thread, per-source engineered feature data for the unstructured feature extraction thread, where the per-source engineered feature data for an unstructured feature extraction thread may include a collection of structured data objects generated by processing the corresponding per-source unstructured feature data for the unstructured feature extraction thread using the shared feature processing interface.

The shared feature processing interface may include a collection of computer-implemented processes configured to generate inferred structured data based on input unstructured data. An example of a shared feature processing interface is a shared natural language processing (NLP) engine comprising one or more NLP processes configured to generate inferred structured data based on input unstructured natural language data. For example, a shared NLP engine may be configured to extract metadata (e.g., associated patient identifiers, associate diagnosis codes, associated operational codes, and/or the like) from natural language medical note documents.

In some embodiments, step/operation 503 may be performed on a per-unstructured-thread level in accordance with the process depicted in FIG. 6. As depicted in FIG. 6, at step/operation 601, an unstructured feature extraction thread determines a feature-relevant subset of per-source unstructured feature data for the particular unstructured feature extraction thread. The feature-relevant subset of the per-source unstructured feature data for the unstructured feature extraction thread may be a collection of data objects from the per-source unstructured feature data that are deemed with certainty to be associated with an input entity subject to the data evaluation. For example, a feature relevant subset may include medical note documents that are deemed with certainty to be associated with a patient input entity subject to the data evaluation.

At step/operation 602, the particular unstructured feature extraction thread determines a potentially feature-relevant subset of per-source unstructured feature data for the unstructured feature extraction thread. The potentially feature-relevant subset of the per-source unstructured feature data for the unstructured feature extraction thread may be a collection of data objects from the per-source unstructured feature data that are deemed with some degree of uncertainty to be associated with an input entity subject to the data evaluation. For example, a feature relevant subset may include medical note documents that are deemed with some degree of uncertainty to be associated with a patient input entity subject to the data evaluation.

At step/operation 603, the unstructured feature extraction thread generates per-source engineered feature data for the unstructured feature extraction thread based on at least one of the feature-relevant subset for the unstructured feature extraction thread and the potentially feature-relevant subset for the unstructured feature extraction thread. In some embodiments, the unstructured feature extraction thread combines the feature-relevant subset for the unstructured feature extraction thread and at least a portion of the potentially feature-relevant subset for the unstructured feature extraction thread to generate the per-source engineered feature data for the unstructured feature extraction thread.

In some embodiments, step/operation 603 may be performed in accordance with the process depicted in FIG. 7. As depicted in FIG. 7, at step/operation 701, the unstructured feature extraction thread determines confirmation data for the potentially feature-relevant subset. The confirmation data may include a collection of data objects that describe, for each data object in the potentially feature-relevant subset, whether association of the data object with an input entity subject to the data evaluation has been confirmed by a secondary authority (e.g., a secondary authority using human-generated data, such as physician confirmatory data, provider confirmatory data, insurance confirmatory data, and/or the like).

At step/operation 702, the unstructured feature extraction thread identifies a confirmed subset of potentially-relevant subset based on the confirmation data. In some embodiments, the confirmed subset includes each potentially relevant data object in the potentially-relevant subset whose association with an input entity subject to the data evaluation has been confirmed by at least one data object in the confirmation data. In some embodiments, the confirmed subset includes each potentially relevant data object in the potentially-relevant subset whose association with an input entity subject to the data evaluation has been confirmed by a predefined threshold number of data objects in the confirmation data. In some embodiments, the confirmed subset includes each potentially relevant data object in the potentially-relevant subset whose association with an input entity subject to the data evaluation has been confirmed by a predefined threshold ratio of data objects in the confirmation data. In some embodiments, the confirmed subset includes each potentially relevant data object in the potentially-relevant subset whose association with an input entity subject to the data evaluation has been confirmed by a predefined threshold ratio of data objects related to the potentially relevant data object in the confirmation data.

At step/operation 703, the unstructured feature extraction thread generates the per-source engineered feature data for the unstructured feature extraction thread based on the feature-relevant subset for the unstructured feature extraction thread and the confirmed subset of the potentially feature-relevant subset the unstructured feature extraction thread. In some embodiments, the unstructured feature extraction thread combines the following two sets of unstructured data objects in order to generate an aggregated set of unstructured data objects deemed related to an input entity subject to the data evaluation: (i) the set of unstructured data objects (e.g., medical note documents) deemed with certainty to be related to the input entity; and (ii) the set of unstructured data objects deemed with some degree of uncertainty to be related to an input entity subject to the data evaluation and who have been confirmed by the confirmation data in order to provide a selected set of unstructured data objects deemed. Thereafter, the unstructured feature extraction thread may utilize the aggregated set of unstructured data objects to generate per-source engineered feature data for the unstructured feature extraction thread.

Returning to FIG. 5, at step/operation 504, the feature extraction engine 401 aggregates each per-source retrieved feature data extracted by a structured feature extraction thread of the one or more structured feature extraction threads and each per-source engineered feature data generated by an unstructured feature extraction thread of the one or more unstructured feature extraction threads to generate the shared evidentiary data 411. In some embodiments, the feature extraction engine 401 combines structured data retrieved from structured data sources by structured feature extraction threads and engineered structured data generated based on unstructured data retrieved unstructured data sources by unstructured feature extraction threads to generate the per-source retrieved feature data.

An operational example of a process 1100 for thread coordination by the feature extraction engine 401 is depicted in FIG. 11. As depicted in FIG. 11, the feature extraction engine 401 causes each structured feature extraction thread 1101A-N to retrieve structured data from a respective structured data source 1102A-N. For example, the feature extraction engine 401 causes the structured feature extraction thread 1101A to retrieve structured data from a respective structured data source 1102A, the structured feature extraction thread 1101B to retrieve structured data from a respective structured data source 1102B, and the structured feature extraction thread 1101N to retrieve structured data from a respective structured data source 1102N.

Furthermore, the feature extraction engine 401 causes each unstructured feature extraction thread 1103A-N to retrieve unstructured data from a respective unstructured data source 1104A-N and to process the retrieved structured data using a shared feature processing interface 1105 to generate corresponding engineered structured data.

For example, the feature extraction engine 401 causes the unstructured feature extraction thread 1103A to retrieve unstructured data from a respective unstructured data source 1104A and to process the retrieved structured data using a shared feature processing interface 1105 to generate corresponding engineered structured data. As another example, the feature extraction engine 401 causes the unstructured feature extraction thread 1103B to retrieve unstructured data from a respective unstructured data source 1104B and to process the retrieved structured data using a shared feature processing interface 1105 to generate corresponding engineered structured data. As a further example, the feature extraction engine 401 causes the unstructured feature extraction thread 1103N to retrieve unstructured data from a respective unstructured data source 1104N and to process the retrieved structured data using a shared feature processing interface 1105 to generate corresponding engineered structured data.

Moreover, the feature extraction engine 401 may in some embodiments cause each unstructured feature extraction thread 1103A-N to generate the engineered structured data generated for the unstructured feature extraction thread 1103A-N to the feature extraction engine 401.

For example, the feature extraction engine 401 causes the unstructured feature extraction thread 1103A to generate the engineered structured data generated for the unstructured feature extraction thread 1103A to the feature extraction engine 401. As another example, the feature extraction engine 401 causes the unstructured feature extraction thread 1103B to generate the engineered structured data generated for the unstructured feature extraction thread 1103B to the feature extraction engine 401. For example, the feature extraction engine 401 causes the unstructured feature extraction thread 1103N to generate the engineered structured data generated for the unstructured feature extraction thread 1103N to the feature extraction engine 401.

Returning to FIG. 4, subsequent to generating the shared evidentiary data 411, the feature extraction engine 401 provides the shared evidentiary data 411 to the evidence refinement engine 402 of the data evaluation computing entity 106. The evidence refinement engine 402 is configured to refined evidentiary data 412 based on a selected evidentiary data subset of the shared evidentiary data 411 that correspond to one or more selected nodes of the shared decision tree data object. The shared decision tree data object may be a data object that describes one or more evaluation criteria for a particular data evaluation. The shared decision tree data object may further be associated with a sufficiency criterion that describes one or more combinations of the evaluation criteria described by the shared decision tree data object that satisfy the requirements of the particular data evaluation associated with the shared decision tree data object.

For example, a shared decision tree data object may have five evaluation criteria $EC_1$, $EC_2$, $EC_3$, $EC4_4$, and $EC_5$. An example sufficiency criterion for the shared decision tree data object may describe that, to satisfy the requirements of the particular data evaluation associated with the shared decision tree data object, the refined evidentiary data must satisfy at least three of the noted five evaluation criteria. Another example sufficiency criterion for the shared decision tree data object may describe that, to satisfy the requirements of the particular data evaluation associated with the shared decision tree data object, the refined evidentiary data must satisfy either at least three of the noted five evaluation criteria if the refined evidentiary data does not satisfy the first evaluation criterion $EC_1$ and at least two of the noted five evaluation criteria if the refined evidentiary data satisfies the first evaluation criterion $EC_1$. A yet another example sufficiency criterion for the shared decision tree data object may describe that, to satisfy the requirements of the particular data evaluation associated with the shared decision tree data object, the refined evidentiary data must satisfy the first evaluation criterion $EC_1$ and at least three other evaluation criteria of the five noted evaluation criteria. A further example sufficiency criterion for the shared decision tree data object may describe that, to satisfy the requirements of the particular data evaluation associated with the shared decision tree data object, the refined evidentiary data must satisfy both of at least one of the first evaluation criterion $EC_1$ and the second evaluation criterion $EC_2$ and at least two other evaluation criteria of the five noted evaluation criteria.

An operational example of evaluation criteria data object 1200 that can be used to generate a shared decision tree data object is presented in FIG. 12. As depicted in FIG. 12, the evaluation criteria data object 1200 include nine evaluation-criteria-related segments 1201 and two sufficiency-criterion-related portions 1202. In some embodiments, the data evaluation computing entity 106 may utilize the evaluation criteria data object 1200 to generate a shared decision tree data objects with nine leaf nodes corresponding to the nine evaluation-criteria-related segments 1201 of the evaluation criteria data object 1200 and a sufficiency criterion indicating that at least one of the nine leaf nodes must be met for the shared decision tree data object to be deemed satisfied. In some embodiments, the data evaluation computing entity 106 may combine evaluation criteria information from two or more evaluation criteria data objects to generate a shared evaluation data object. In some embodiments, the data evaluation computing entity 106 may receive the shared decision tree data object from a client computing entity 102 and/or from an external computing entity.

The refined evidentiary data 412 may include a subset of the shared evidentiary data 411 that correspond to the evaluation criteria described by the shared decision tree data object for the data evaluation. In some embodiments, generating the refined evidentiary data comprises identifying, based on the shared decision tree data object, one or more evaluation criterion data objects, wherein each evaluation criterion data object of the one or more evaluation criterion data objects corresponds to a selected node of the selected nodes of the shared decision tree data object; determining a classification-relevant subset of the shared evidentiary data that correspond to the one or more evaluation criterion data objects; and generating the refined evidentiary data based on the classification-relevant subset.

After generating the refined evidentiary data 412, the evidence refinement engine 402 provides the refined evidentiary data 412 to the evaluation engine 403 of the data evaluation computing entity 106. The evaluation engine 403 may be configured to process the refined evidentiary data in accordance with the shared decision tree data object to generate an evaluation output 413 and an explanation output 414.

The evaluation output 413 may be a data object that indicates whether the input entity subject to the data evaluation satisfies the requirements of the data evaluation. To generate the evaluation output 413, the evidence refinement engine 402 may determine whether the refined evidentiary data 412 satisfy the requirements described by the evaluation criteria of the shared decision tree data object and the sufficiency criterion of the shared decision tree data object. In some embodiments, the input entity is a patient input entity, the shared evidentiary data comprises medical history data of the patient input entity, the shared decision tree data object describes authorization criteria for a proposed medical operation, and the evaluation output describes an authorization determination for the proposed medical operation with respect to the patient input entity.

In some embodiments, the evaluation engine 403 may generate the evaluation output 413 in accordance with the various steps/operations of the process depicted in FIG. 8. As depicted in FIG. 8, at step/operation 801, the evaluation engine 403 determines a per-criterion evaluation for each evaluation criterion of one or more evaluation criteria described by the shared decision tree data object based on the refined evidentiary data 412. The per-criterion evaluation for an evaluation criterion may be a data object that describes whether the refined evidentiary data 412 provides sufficient evidence indicating that the evaluation criterion has been satisfied.

For example, if an evaluation criterion requires history of heart failure, the per-criterion evaluation for the evaluation criterion may indicate whether refined evidentiary data 412 describing medical history of a corresponding patient input entity describes a history of heart failure in relation to the corresponding patient input entity. As another example, if an evaluation criterion requires chronic kidney disease, the per-criterion evaluation for the evaluation criterion may indicate whether refined evidentiary data 412 describing medical condition of a corresponding patient input entity describes chronic kidney disease in relation to corresponding patient input entity. As yet another example, if an evaluation criterion requires at least 45 years of age, the per-criterion evaluation for the evaluation criterion may indicate whether refined evidentiary data 412 describing demographic information of a corresponding patient input entity describes that the corresponding patient input entity is at least 45 years of age.

At step/operation 802, the evaluation engine 403 a positive evaluation subset of the one or more evaluation criteria described by the shared decision tree data object based on each per-criterion evaluation for an evaluation criterion of the one or more evaluation criteria. In some embodiments, the positive evaluation subset comprises each evaluation criteria described by the shared decision tree data object that the refined evidentiary data 412 indicates as having been satisfied by the shared evidentiary data 411.

For example, in some embodiments, if an evaluation criterion requires chronic kidney disease, and further if the per-criterion evaluation for the evaluation criterion indicates that refined evidentiary data 412 describes that a corresponding patient input entity has chronic kidney disease, the evaluation criteria will be in the positive evaluation subset of the one or more evaluation criteria described by the shared decision tree data object. As another example, if an evaluation criterion requires at least 45 years age, and further if the per-criterion evaluation for the evaluation criterion indicates that refined evidentiary data 412 describes that a corresponding patient input entity is 55 years of age, the evaluation criteria will be in the positive evaluation subset of the one or more evaluation criteria described by the shared decision tree data object.

At step/operation 803, the evaluation engine 403 generates the evaluation output 413 based on whether the positive evaluation subset satisfies a sufficiency criterion for the shared decision tree data object. In some embodiments, the sufficiency criterion is a data object describes a threshold count of evaluation criteria described by the shared decision tree data object. In some of the noted embodiments, the evaluation output 413 describes whether the count of evaluation criteria in the positive evaluation subset satisfies the threshold count of evaluation criteria described by the sufficient criterion. In some embodiments, the sufficiency criterion is a data object describes one or more acceptable evaluation criteria combinations. In some of the noted embodiments, the evaluation output 413 describes whether at least one of the evaluation criteria in the positive evaluation subset corresponds to at least one of the one or more acceptable evaluation criteria combinations described by the sufficient criterion. In some embodiments, the sufficiency criterion is a data object describes one or more required properties of acceptable evaluation criteria combinations. In some of the noted embodiments, the evaluation output 413 describes whether at least one of the evaluation criteria in the positive evaluation subset satisfies at least one of the one or more required properties of acceptable evaluation criteria combinations described by the sufficient criterion.

The explanation output 414 may be a data object that describes at least one mapping between at least a portion of the shared evidentiary data 411 and at least a portion of the evaluation criteria described by the shared decision tree data object. For example, the explanation output 414 may describe which portions of the refined evidentiary data 412 are used as support to reach a determination that a corresponding input entity has satisfied a particular evaluation criterion described by the shared decision tree data object and/or has failed to satisfy a particular evaluation criterion described by the shared decision tree data object. As another example, the explanation output 414 may describe which evaluation criteria described by the shared decision tree data object have been satisfied by the refined evidentiary data 412 and/or which evaluation criteria described by the shared decision tree data object have not been satisfied by the refined evidentiary data 412.

In some embodiments, the evaluation engine 403 may generate the explanation output 414 in accordance with the various steps/operations of the process depicted in FIG. 9. As depicted in FIG. 9, at step/operation 901, the evaluation engine 403 determines a per-criterion evaluation for each evaluation criterion of one or more evaluation criteria described by the shared decision tree data object based on the refined evidentiary data 412. The per-criterion evaluation for an evaluation criterion may be a data object that describes whether the refined evidentiary data 412 provides sufficient evidence indicating that the evaluation criterion has been satisfied.

For example, if an evaluation criterion requires history of heart failure, the per-criterion evaluation for the evaluation criterion may indicate whether refined evidentiary data 412 describing medical history of a corresponding patient input entity describes a history of heart failure in relation to the corresponding patient input entity. As another example, if an evaluation criterion requires chronic kidney disease, the per-criterion evaluation for the evaluation criterion may indicate whether refined evidentiary data 412 describing medical condition of a corresponding patient input entity describes chronic kidney disease in relation to corresponding patient input entity. As yet another example, if an evaluation criterion requires at least 45 years of age, the per-criterion evaluation for the evaluation criterion may indicate whether refined evidentiary data 412 describing demographic information of a corresponding patient input entity describes that the corresponding patient input entity is at least 45 years of age.

At step/operation 902, the evaluation engine 403 identifies a criterion-related subset of the refined evidentiary data 412 for each evaluation criterion of one or more evaluation criteria described by the shared decision tree data object. A criterion-related subset associated with an evaluation criterion may be a data object that describe at least one portion of refined evidentiary data 412 that is determined to include information deemed pertinent to determining whether the refined evidentiary data 412 satisfy the evaluation criterion. For example, if an evaluation criterion relates to medical history, the per-criterion subset for the evaluation criterion may be extracted from the medical history data of a corresponding patient input entity. As another example, if an evaluation criterion relates to prescription history, the per-criterion subset for the evaluation criterion may be extracted from the prescription history data of a corresponding patient input entity. As yet another example, if an evaluation criterion relates to patient age, the per-criterion subset for the evaluation criterion may be extracted from the patient profile data and/or patient demographic data of a corresponding patient input entity.

At step/operation 903, the evaluation engine 403 generates the explanation output 414 based on each per-criterion evaluation for an evaluation criterion and each criterion-related subset for an evaluation criterion. In some embodiments, the evaluation engine 403 combine at least a portion of on each per-criterion evaluation for an evaluation criterion and at least a portion of each criterion-related subset for an evaluation criterion in order to generate the explanation output 414. For example, the evaluation engine 403 may combine all of on each per-criterion evaluation for an evaluation criterion and all of each criterion-related subset for an evaluation criterion in order to generate the explanation output 414.

Returning to FIG. 4, subsequent to generating the evaluation output 413 and the explanation output 414, the evaluation engine 403 provides the evaluation output 413 and the explanation output 414 to the display engine 404. The display engine 404 is configured to display (e.g., using a decoupled user interface module) an evaluation output user interface 415 comprising display data describing the evaluation output and the classification explanation output. In some embodiments, the display engine 404 provides user interface data associated with the evaluation output user interface 415 to a client computing entity 102, where the user interface data may be a collection of data objects that contains display data (e.g., Hyper-Text Markup Language (HTML) data) that can be executed to display the evaluation output user interface 415.

An operational example of the evaluation output user interface 415 is presented in FIG. 10. As depicted in FIG. 10, the evaluation output user interface 415 of FIG. 10 displays the evaluation output 1001 at the top-right edge of the evaluation output user interface 415 and the data evaluation subject matter 1002 at the top-center of the evaluation output user interface 415.

As further depicted in FIG. 10, the evaluation output user interface 415 of FIG. 10 displays per-criterion evaluations for relevant evaluation criteria in the main region 1003 of the evaluation output user interface 415. Selecting an interactive portion of a per-criterion-evaluation such as the per-criterion evaluation 1004 may lead to display of information associated with the per-criterion-evaluation, such as the relevant diagnosis code information 1005 for an evaluation criterion associated with the per-criterion evaluation 1004 and criterion-related evidentiary data objects 1006 for the evaluation criterion associated with the per-criterion evaluation 1004. Moreover, selecting an interactive portion of a criterion-related evidentiary data object such as the criterion-related evidentiary data 1007 may lead to display of information associated with the criterion-related evidentiary data, such as a text version and/or an image version of the criterion-related evidentiary data 1007.

In some embodiments, the data evaluation computing entity 106 may perform one or more evaluation-based actions based on at least one of the evaluation output 413 and the explanation output 414. For example, the data evaluation computing entity 106 may grant and/or deny pre-authorization for a proposed medical operation based on the evaluation output 413. Other examples of evaluation-based actions that may be performed by the data evaluation computing entity 106 include automatic generating of pre-authorization approval notifications, automatic generating of pre-authorization denial notifications, automatic scheduling of pre-authorization-related consultation meetings, automatic scheduling of pre-authorization secondary review tasks, and/or the like.

Accordingly, as described above, the parallelized data evaluation concepts of the present invention can be utilized to perform efficient and reliable data evaluation in a variety of contexts, such as the in the context of performing prior authorization of proposed medical operations in relation to patient needs. For example, in some embodiments, the data evaluation computing entity 106 may extract (e.g., using a parallelized data extraction procedure) evidentiary data describing patient history and/or patient demographics of a patient that is subject of a prior authorization task, refine the extracted evidentiary data in accordance with a decision tree data object that describes the pre-authorization requirements for generating a positive prior authorization determination for the noted prior authorization task in order to isolate portions of the extracted evidentiary that relate to the noted pre-authorization requirements, process the refined evidentiary data in accordance with the decision tree data object in order to determine a prior authorization determination for the proposed medical operation, aggregate the refined evidentiary data used to reach the prior authorization determination to generate an explanation output for the prior authorization determination, and present display data related to the prior authorization determination and the explanation output using a prior authorization user interface configured to display prior-authorization-related data to end-users (e.g., to physicians, nurses, hospital staff, and/or the like).

The process 400 further includes managing the operations of the feature extraction engine 401, the evidence refinement engine 402, the evaluation engine 403, and the display engine 404 using a conductor 420 of the data evaluation computing entity 106. In some embodiments, the conductor 420 is configured to coordinate sequential operation of various operations of the process 400, including at least one of the following: (i) retrieval of structured data associated with an input entity (e.g., a patient entity) from structured data sources using parallel execution of structured feature extraction threads; (ii) retrieval of unstructured data from unstructured data sources associated with an input entity using parallel execution of unstructured feature extraction threads; (iii) pre-processing of retrieved unstructured data to generate engineered feature data using parallel execution of unstructured feature extraction threads; (iv) generation of evidentiary data by the feature extraction engine 401 (e.g., using one or more parallel execution threads) based on retrieved structured data and engineered data generated by performing pre-processing on retrieved unstructured data; (v) transfer of evidentiary data generated by the feature extraction engine 401 to the evidence refinement engine 402; (vi) refinement of evidentiary data by the evidence refinement engine 402 (e.g., using one or more parallel execution threads) to generate refined evidentiary data; (vii) transfer of refined evidentiary data generated by the evidence refinement engine 402 to the evaluation engine 403; (viii) generation of evaluation outputs and/or explanation outputs by the evaluation engine 403 (e.g., using one or more parallel execution threads) based on the refined evidentiary data; (ix) transfer of evaluation outputs and/or explanation outputs generated by the evaluation engine 403 to the display engine 404; and (x) generation of the evaluation output user interfaces by the display engine 404.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
    generating, by one or more processors and using a plurality of feature extraction threads, shared evidentiary data, wherein generating the shared evidentiary data comprises:
        identifying one or more structured feature extraction threads of the plurality of feature extraction threads and one or more unstructured feature extraction threads of the plurality of feature extraction threads;
        causing each structured feature extraction thread of the one or more structured feature extraction threads to extract corresponding per-source retrieved feature data from a corresponding structured data source that is associated with the structured feature extraction thread;
        causing each unstructured feature extraction thread of the one or more unstructured feature extraction threads to (i) extract corresponding per-source unstructured feature data from a corresponding unstructured data source that is associated with the unstructured feature extraction thread, and (ii) generate per-source engineered feature data for the unstructured feature extraction thread based at least in part on the corresponding per-source unstructured feature data for the unstructured feature extraction thread; and
        generating shared evidentiary data by aggregating each per-source retrieved feature data extracted by a structured feature extraction thread and each per-source engineered feature data generated by an unstructured feature extraction thread;
    generating, by the one or more processors and based at least in part on a selected shared evidentiary data subset of the shared evidentiary data that correspond to one or more selected nodes of a shared decision tree data object, refined evidentiary data;
    generating, by the one or more processors, an evaluation output and an explanation output based at least in part on the refined evidentiary data and the shared decision tree data object; and
    providing, by the one or more processors and for display via a user interface, at least a portion of the evaluation output comprising user interface data indicative of the evaluation output and the explanation output.

2. The computer-implemented method of claim 1, wherein generating the per-source engineered feature data for an unstructured feature extraction thread of the one or more structured feature extraction threads comprises:
    determining, by the unstructured feature extraction thread, a feature-relevant subset of the corresponding per-source unstructured feature data for the unstructured feature extraction thread and a potentially feature-relevant subset of the corresponding per-source unstructured feature data for the unstructured feature extraction thread; and generating, by the unstructured feature extraction thread, the per-source engineered feature data for the unstructured feature extraction thread based at least in part on at least one of the feature-relevant subset of the corresponding per-source unstructured feature data and the potentially feature-relevant subset of the corresponding per-source unstructured feature data.

3. The computer-implemented method of claim 2, wherein generating the per-source engineered feature data for the unstructured feature extraction thread based at least in part on at least one of the feature-relevant subset and the potentially feature-relevant subset comprises:
   determining, by the unstructured feature extraction thread, confirmation data for the potentially feature-relevant subset;
   identifying, by the unstructured feature extraction thread, a confirmed subset of the potentially feature-relevant subset based at least in part on the confirmation data; and
   generating, by the unstructured feature extraction thread, the per-source engineered feature data based at least in part on the feature-relevant subset and the confirmed subset of the potentially feature-relevant subset.

4. The computer-implemented method of claim 1, wherein the one or more selected nodes of the shared decision tree data object comprise one or more leaf nodes of the shared decision tree data object.

5. The computer-implemented method of claim 1, wherein generating the refined evidentiary data comprises:
   identifying, based at least in part on the shared decision tree data object, one or more evaluation criterion data objects, wherein each evaluation criterion data object of the one or more evaluation criterion data objects corresponds to a selected node of the one or more selected nodes of the shared decision tree data object;
   determining a classification-relevant subset of the shared evidentiary data that correspond to the one or more evaluation criterion data objects; and
   generating the refined evidentiary data based at least in part on the classification-relevant subset.

6. The computer-implemented method of claim 1, wherein generating the evaluation output comprises:
   for each evaluation criterion data object of one or more evaluation criterion data objects described by the shared decision tree data object, determining a per-criterion evaluation based at least in part on the refined evidentiary data;
   identifying a positive evaluation subset of the one or more evaluation criterion data objects based at least in part on each per-criterion evaluation for an evaluation criterion data object of the one or more evaluation criterion data objects; and
   generating the evaluation output based at least in part on whether the positive evaluation subset satisfies a sufficiency criterion for the shared decision tree data object.

7. The computer-implemented method of claim 1, wherein generating the explanation output comprises:
   for each evaluation criterion data object of one or more evaluation criterion data objects, determining a per-criterion evaluation based a corresponding criterion-related subset of the refined evidentiary data; and
   generating the explanation output based at least in part on each per-criterion evaluation for an evaluation criterion data object of the one or more evaluation criterion data objects and each criterion-related subset for an evaluation criterion data object of the one or more evaluation criterion data objects.

8. The computer-implemented method of claim 1, wherein:
   an input entity is a patient input entity;
   the shared evidentiary data comprises medical history data of the patient input entity;
   the shared decision tree data object describes authorization criteria for a proposed medical operation; and
   the evaluation output describes an authorization determination for the proposed medical operation with respect to the patient input entity.

9. A system comprising one or more processors and at least one memory including program code, the at least one memory and the program code configured to, with the one or more processors, cause the system to at least:
   generate, using a plurality of feature extraction threads, shared evidentiary data, wherein generating the shared evidentiary data comprises:
      identifying one or more structured feature extraction threads of the plurality of feature extraction threads and one or more unstructured feature extraction threads of the plurality of feature extraction threads;
      causing each structured feature extraction thread of the one or more structured feature extraction threads to extract corresponding per-source retrieved feature data from a corresponding structured data source that is associated with the structured feature extraction thread;
      causing each unstructured feature extraction thread of the one or more unstructured feature extraction threads to (i) extract corresponding per-source unstructured feature data from a corresponding unstructured data source that is associated with the unstructured feature extraction thread, and (ii) generate per-source engineered feature data for the unstructured feature extraction thread based at least in part on the corresponding per-source unstructured feature data for the unstructured feature extraction thread; and
      generating shared evidentiary data by aggregating each per-source retrieved feature data extracted by a structured feature extraction thread and each per-source engineered feature data generated by an unstructured feature extraction thread;
   generate, based at least in part on a selected shared evidentiary data subset of the shared evidentiary data that correspond to one or more selected nodes of a shared decision tree data object, refined evidentiary data;
   generate an evaluation output and an explanation output based at least in part on the refined evidentiary data and the shared decision tree data object; and
   provide, for display via a user interface, at least a portion of the evaluation output comprising user interface data indicative of the evaluation output and the explanation output.

10. The system of claim 9, wherein generating the per-source engineered feature data for an unstructured feature extraction thread of the one or more structured feature extraction threads comprises:
   determining, by the unstructured feature extraction thread, a feature-relevant subset of the corresponding per-source unstructured feature data for the unstructured feature extraction thread and a potentially feature-relevant subset of the corresponding per-source unstructured feature data for the unstructured feature extraction thread; and generating, by the unstructured feature extraction thread, the per-source engineered feature data for the unstructured feature extraction thread based at least in part on at least one of the feature-relevant subset of the corresponding per-source unstructured feature data and the potentially feature-relevant subset of the corresponding per-source unstructured feature data.

11. The system of claim 10, wherein generating the per-source engineered feature data for the unstructured feature extraction thread based at least in part on at least one of the feature-relevant subset and the potentially feature-relevant subset comprises:

determining, by the unstructured feature extraction thread, confirmation data for the potentially feature-relevant subset;

identifying, by the unstructured feature extraction thread, a confirmed subset of the potentially feature-relevant subset based at least in part on the confirmation data; and generating, by the unstructured feature extraction thread, the per-source engineered feature data based at least in part on the feature-relevant subset and the confirmed subset of the potentially feature-relevant subset.

12. The system of claim 9, wherein the one or more selected nodes of the shared decision tree data object comprise one or more leaf nodes of the shared decision tree data object.

13. The system of claim 9, wherein generating the refined evidentiary data comprises:

identifying, based at least in part on the shared decision tree data object, one or more evaluation criterion data objects, wherein each evaluation criterion data object of the one or more evaluation criterion data objects corresponds to a selected node of the one or more selected nodes of the shared decision tree data object;

determining a classification-relevant subset of the shared evidentiary data that correspond to the one or more evaluation criterion data objects; and generating the refined evidentiary data based at least in part on the classification-relevant subset.

14. The system of claim 9, wherein generating the evaluation output comprises:

for each evaluation criterion data object of one or more evaluation criterion data objects described by the shared decision tree data object, determining a per-criterion evaluation based at least in part on the refined evidentiary data;

identifying a positive evaluation subset of the one or more evaluation criterion data objects based at least in part on each per-criterion evaluation for an evaluation criterion data object of the one or more evaluation criterion data objects; and generating the evaluation output based at least in part on whether the positive evaluation subset satisfies a sufficiency criterion for the shared decision tree data object.

15. The system of claim 9, wherein generating the explanation output comprises:

for each evaluation criterion data object of one or more evaluation criterion data objects, determining a per-criterion evaluation based a corresponding criterion-related subset of the refined evidentiary data; and generating the explanation output based at least in part on each per-criterion evaluation for an evaluation criterion data object of the one or more evaluation criterion data objects and each criterion-related subset for an evaluation criterion data object of the one or more evaluation criterion data objects.

16. The system of claim 9, wherein:

an input entity is a patient input entity;

the shared evidentiary data comprises medical history data of the patient input entity;

the shared decision tree data object describes authorization criteria for a proposed medical operation; and the evaluation output describes an authorization determination for the proposed medical operation with respect to the patient input entity.

17. At least one non-transitory computer-readable storage medium having computer-readable program code portions stored therein, the computer-readable program code portions configured to:

generate, using a plurality of feature extraction threads, shared evidentiary data, wherein generating the shared evidentiary data comprises:

identifying one or more structured feature extraction threads of the plurality of feature extraction threads and one or more unstructured feature extraction threads of the plurality of feature extraction threads;

causing each structured feature extraction thread of the one or more structured feature extraction threads to extract corresponding per-source retrieved feature data from a corresponding structured data source of one or more structured data sources that is associated with the structured feature extraction thread;

causing each unstructured feature extraction thread of the one or more unstructured feature extraction threads to (i) extract corresponding per-source unstructured feature data from a corresponding unstructured data source of one or more unstructured data sources that is associated with the unstructured feature extraction thread, and (ii) generate per-source engineered feature data for the unstructured feature extraction thread based at least in part on the corresponding per-source unstructured feature data for the unstructured feature extraction thread; and generating shared evidentiary data by aggregating each per-source retrieved feature data extracted by a structured feature extraction thread and each per-source engineered feature data generated by an unstructured feature extraction thread;

generate, based at least in part on a selected shared evidentiary data subset of the shared evidentiary data that correspond to one or more selected nodes of a shared decision tree data object, refined evidentiary data;

generate an evaluation output and an explanation output based at least in part on the refined evidentiary data and the shared decision tree data object; and provide, for display via a user interface, at least a portion of the evaluation output comprising user interface data indicative of the evaluation output and the explanation output.

18. The at least one non-transitory computer-readable storage medium of claim 17, wherein generating the per-source engineered feature data for an unstructured feature extraction thread of the one or more structured feature extraction threads comprises:

determining, by the unstructured feature extraction thread, a feature-relevant subset of the corresponding per-source unstructured feature data for the unstructured feature extraction thread and a potentially feature-relevant subset of the corresponding per-source unstructured feature data for the unstructured feature extraction thread; and generating, by the unstructured feature extraction thread, the per-source engineered feature data for the unstructured feature extraction thread based at least in part on at least one of the feature-relevant subset of the corresponding per-source unstructured feature data and the potentially feature-relevant subset of the corresponding per-source unstructured feature data.

19. The at least one non-transitory computer-readable storage medium of claim 18, wherein generating the per-source engineered feature data for the unstructured feature extraction thread based at least in part on at least one of the feature-relevant subset and the potentially feature-relevant subset comprises:

determining, by the unstructured feature extraction thread, confirmation data for the potentially feature-relevant subset;

identifying, by the unstructured feature extraction thread, a confirmed subset of the potentially feature-relevant subset based at least in part on the confirmation data; and generating, by the unstructured feature extraction thread, the per-source engineered feature data based at least in part on the feature-relevant subset and the confirmed subset of the potentially feature-relevant subset.

20. The at least one non-transitory computer-readable storage medium of claim 17, wherein:

an input entity is a patient input entity;

the shared evidentiary data comprises medical history data of the patient input entity;

the shared decision tree data object describes authorization criteria for a proposed medical operation; and the evaluation output describes an authorization determination for the proposed medical operation with respect to the patient input entity.

* * * * *